(12) United States Patent
Stopek

(10) Patent No.: US 8,486,047 B2
(45) Date of Patent: Jul. 16, 2013

(54) PACKAGED MEDICAL DEVICE

(75) Inventor: Joshua Stopek, Yalesville, CT (US)

(73) Assignee: Covidien LP, Mansfield, MA (US)

( * ) Notice: Subject to any disclaimer, the term of this patent is extended or adjusted under 35 U.S.C. 154(b) by 246 days.

(21) Appl. No.: 11/799,965

(22) Filed: May 3, 2007

(65) Prior Publication Data

US 2008/0272012 A1 Nov. 6, 2008

(51) Int. Cl.
*A61M 25/00* (2006.01)
(52) U.S. Cl.
USPC .......................................... 604/523; 604/533
(58) Field of Classification Search
USPC ......... 206/63.3; 604/523, 174–180, 500–522, 604/533–284
See application file for complete search history.

(56) References Cited

U.S. PATENT DOCUMENTS

| | | |
|---|---|---|
| 4,024,871 A | 5/1977 | Stephenson |
| 4,925,448 A | 5/1990 | Bazaral |
| 5,111,836 A | 5/1992 | Grabenkort |
| 5,385,229 A | 1/1995 | Bittmann et al. |
| 5,454,798 A * | 10/1995 | Kubalak et al. ............... 604/328 |
| 5,462,162 A * | 10/1995 | Kaplan et al. .................. 206/339 |
| 6,106,505 A | 8/2000 | Modak et al. |
| 6,135,272 A * | 10/2000 | Sobel et al. ................... 206/63.3 |
| 2005/0278012 A1* | 12/2005 | Vonderwalde ............... 623/1.11 |
| 2007/0170080 A1* | 7/2007 | Stopek et al. .................. 206/438 |

FOREIGN PATENT DOCUMENTS

| | | |
|---|---|---|
| EP | 0 499 048 A1 | 8/1992 |
| EP | 0 647 452 A1 | 4/1995 |
| EP | 1813220 | 8/2007 |
| WO | WO9706733 | 2/1997 |
| WO | WO9937233 | 7/1999 |
| WO | WO 9937233 A1 * | 7/1999 |
| WO | WO 00/57933 A1 | 10/2000 |

OTHER PUBLICATIONS

International Search Report from Application EP 06 01 2688 dated Aug. 1, 2007.
European Search Report for EP 08251582.6-2310 date of completion is Aug. 17, 2009 (4 pages).

* cited by examiner

*Primary Examiner* — Bhisma Mehta
*Assistant Examiner* — Phillip Gray

(57) ABSTRACT

The present disclosure provides a packaged medical device including a container for receiving a medical device having a passageway defined therein and a port for permitting the sterile passage of an agent between the outside of the container and the passageway defined within the medical device.

10 Claims, 1 Drawing Sheet

PACKAGED MEDICAL DEVICE

BACKGROUND

1. Technical Field

The present disclosure relates generally to packaging for medical devices, and more particularly, to a packaged medical device including a container configured to receive a medical device having a passageway defined therein and a port in fluid communication with the passageway for permitting the sterile passage of an agent between the outside of the container and the passageway defined within the medical device.

2. Background of Related Art

The concept of medical devices containing a passageway defined therein is known and includes such medical devices as stents, monofilament sutures, multifilament sutures, surgical meshes, adhesion barriers, vascular grafts, cannulas, trocars, catheters, staples, screws, pins, rods, and the like.

In particular, several U.S. patents disclose wound closure devices, e.g., sutures, which contain at least one passageway defined therein. Some non-limiting examples include U.S. Pat. Nos.: 3,918,455; 4,159,720; 5,984,933; and 6,264,600. The passageway defined within the medical device is used for a variety of reasons including facilitating the attachment of a surgical needle and the addition of an agent to be delivered to the implant site or enhance the suture's handling abilities, e.g., knot-tying or lubricity.

Presently, the addition of an agent into the passageway defined within the medical device is completed either prior to being sealed within a sterile package during manufacturing of the medical device, or after being removed from the sterile package during the implantation procedure. Each option has limitations. The addition of an agent prior to packaging limits the choice of agent which may be added to the passageway defined within the medical device, but maintains the sterility of the device. The addition of an agent after removing the device from the sterile package during the implantation procedure allows for the addition of many more agents, but increases the likelihood of contamination of the medical device. It would be advantageous to have a package for receiving a medical device having a passageway defined therein which maintained sterility while allowing for the addition of any agent into the passageway of a medical device.

Therefore, the present disclosure describes a package for receiving a medical device having at least one passageway defined therein, aimed at simplifying the addition of any agent to the inside of the passageway of the medical device, as well as maintaining the sterile conditions in which the addition of the agent is conducted.

SUMMARY

Accordingly, a package for a medical device in accordance with the present disclosure includes a container for receiving a medical device having at least one passageway defined therein and a port positioned on the package and in fluid communication with the passageway for permitting the passage of at least one agent between the outside of the container and the passageway defined within the medical device. The passageway may be defined within any portion of the medical device.

In another embodiment, a medical device package as described herein may include a container configured for receiving a medical device having a passageway defined therein and a plurality of ports positioned on the package and in fluid communication with the passageway for permitting the passage of an agent between the outside of the container and the passageway defined within the medical device.

BRIEF DESCRIPTION OF THE DRAWINGS

Various embodiments are described herein with reference to the drawings wherein.

DETAILED DESCRIPTION

Figure 1:
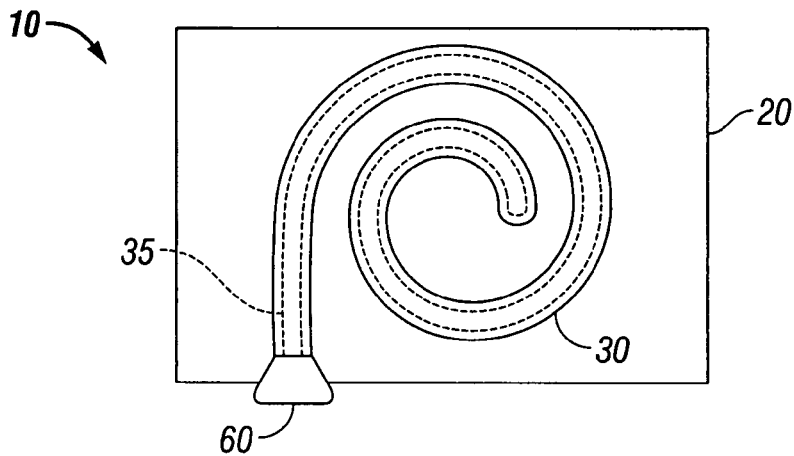
FIG. 1 is a top view of a medical device package as described herein.

The medical device packages described herein include a container having an area configured for receiving a medical device having a passageway defined therein and a port positioned on the package, the port being in fluid communication with the passageway for permitting the passage of an agent between the outside of the container and the passageway defined within the medical device. In some embodiments, the container may include a plurality of ports and/or a plurality of medical devices.

It is envisioned that any medical device having at least one passageway defined therein may be stored within the package. Some examples include, but are not limited to, sutures, staples, clips, stents, grafts, meshes, sternum closures, catheters, microcatheters, pins, screws, tacks, adhesion barriers, buttresses, drug delivery devices, pacemakers, cannulas, surgical implants, and the like. In some embodiments, the medical device is a suture or a surgical mesh.

The medical devices may be made from any bioabsorbable materials or non-absorbable materials, including but not limited to polypropylene, polyamides, polyethyleneterephthalate (PET), polytetraflouroethylene (PTFE), silk, polycaprolactone, polydioxanone, polyglycolide, polylactide, or blends of polycaprolactone, polydioxanone, polyglycolide or polylactide. The medical devices may also be formed using any known methods for forming medical devices including, but not limited to, weaving, braiding, extruding, melting, molding, and the like.

The medical device includes at least one passageway defined therein. The passageway is configured to allow the medical device to receive an agent or agents in a manner which permits the agent to coat, impregnate, extrude from, react with, be absorbed by or be stored within the medical device. In other embodiments, the passageway may be defined within the entire medical device (see FIG. 1). In embodiments, the passageway may be defined within only a portion of the medical device (see FIG. 2). In still other embodiments, the medical device may include more than one passageway, wherein the passageways are configured and designed to permit the passage of at least one agent to different portions of the medical device (see FIG. 3).

Any suitable method of forming a passageway in the medical device may be used. The passageway may be formed in the medical device during or after the formation of the medical device. It is envisioned that the passageway may be configured into any shape, size or dimension. In embodiments, the passageway is dimensioned to fit within the port. In embodiments, the port is dimensioned to fit within the passageway.

In some embodiments the passageway is formed through weaving or braiding multifilaments together around a central bore creating a passageway defined adjacent the center of the braided device. In some embodiments, the passageway is carved into a medical device using a sharpened blade, knife, lathe, laser, drilling device and the like to remove material from the medical device to create a passageway defined therein. In still other embodiments, the passageway may be chemically etched into the medical device.

In some embodiments, the passageway may split into multiple passageways within the medical device. The additional passageways may lead to different interior or exterior portions of the medical device. In embodiments wherein the passageways are defined within the medical device and lead to the exterior surface, the medical device may be used to deliver one or more agents to the site of implantation. It is envisioned that the medical devices described herein may also be useful in radiation treatments, such as brachytherapy, vascular treatments, including embolisms and blood clotting issues.

The container is dimensioned and configured to receive one or more medical devices having at least one passageway defined therein. The container may be any conventional enclosure for storing medical devices and more than one container may be combined to form the medical device packages described herein. Some examples of useful containers include, but are not limited too, pouches, paper retainers, plastic retainers, bags, trays, envelopes, Tyvek® bags, foil-packs, and the like. It is envisioned that the containers may be sealable, non-sealable, breathable, non-breathable, peelable, resealable, and combinations thereof.

The container may be manufactured from any material known to those skilled in the art which is suitable for receiving or storing medical devices. Some examples of suitable materials include, but are not limited to, polycarbonate, high-density polyethylene, polyethylene, polypropylene, thermoplastic elastomers, thermosets, thermoplastic resins, poly(ethylene terephthalate), polytetrafluoroethylene, ε-caprolactone, glycolide, 1-lactide, d,1-lactide, d-lactide, meso-lactide, trimethylene carbonate, 4,4-dimethyl-1,3-dioxan-2-one, p-dioxanone, dioxepanone, δ-valerolactone, β-butyrolactone, ε-decalactone, 2,5-diketomorpholine, pivalolactone, α,α-diethylpropiolactone, 6,8-dioxabicyclooctan-7-one, ethylene carbonate, ethylene oxalate, 3-methyl-1,4-dioxane-2,5-dione, 3,3-dimethyl-1,4-dioxane-2,5-dione, polyolefins, polysiloxanes, polyalkylene glycols, polyacrylates, aminoalkyl acrylates, polyvinylalcohols, polyvinylpyrrolidones, polyoxyethylenes, polyacrylamides, poly(2-hydroxy-ethylmethacrylate), polymethacrylamide, dextran, alginic acid, sodium alginate, polysaccharides, gelatin and copolymers, homopolymers, and block copolymers thereof.

In addition to the container and the medical device having a passageway defined therein, the package includes at least one port. The port is positioned on the package or container in a manner which allows access to the port without having to necessitate the opening of the package thereby maintaining the sterility of the medical device positioned within the container. The port is also in fluid communication with the passageway defined within the medical device, e.g., a hollow suture, in a manner which allows fluid into the passageway from outside of the container or package and through the port without compromising the sterile nature of the medical device, the agent and the package. The port is designed to permit the passage of at least one agent between the outside of the container and the passageway defined within the medical device.

It is envisioned that the port may be any type of port or hub, known to allow the passage of an agent therethrough. The port may be made of any size, shape or dimension capable of being positioned on the package while remaining connected to the passageway defined within the medical device. It is envisioned that the port may be composed of any rubber, gel, metallic, polymeric, or thermoplastic material known to those skilled in the art including polyvinyl chlorides, polyurethanes, polyesters, polyolefins, polyamides, polycarbonates and metal alloys. The port may also be sealable, non-sealable, resealable, stationary, movable, peelable, self-puncturable and combinations thereof.

The port may be positioned along any exterior side, edge or corner of the container. In embodiments wherein the package includes more than one container, the port may be positioned along any side, edge or corner of any of the containers included in the package. In addition, the package may contain more than one port and/or more than one container may share a common port.

In some embodiments, the port may be an injectable-hub, or injection port, which is designed to remain sealed by self-sealing action to ensure no liquid, semi-solid, or gas medium can escape and also so no pathogens can breach the container. In some embodiments, the port may be a hub designed in such a way that only a particular injector can mate with the port, e.g., male/female or lock/key type hubs. These types of ports provide more safety to the user of the port because the port does not necessarily require the use of a sharp injector or needle.

It is envisioned that the port may be permanently attached or removably attached to the medical device. It is further envisioned that the port may be permanently attached or removably attached to the package.

In some embodiments, the port and the medical device may be removed from the package as a single unit and implanted into tissue. The port may be positioned on the exterior of the tissue for accessing while the medical device remained implanted. In embodiments, such as these, the medical device and port could be used as a drug delivery device.

In still other embodiments, the port may be separated from the passageway of the medical device after an agent has been delivered to the passageway and he medical device may be implanted without the port.

The agent is intended to be delivered from outside the container, via the port, to the passageway defined within the medical device. The term "agent" is meant to include any bioactive or non-bioactive material suitable for combination with the medical device. The agent may be in any form including for example solid, liquid, semi-solid, gas, or any combination thereof. Suitable agents include, but are not limited to, drugs, such as antiseptics, anesthetics, muscle relaxants, antihistamines, decongestants, antimicrobial agents, anti-viral agents, anti-fungal agents, antimalarials, amebicides, antituberculosal agents, antiretroviral agents, leprostatics, antiprotazoals, antihelmitics, antibacterial agents, steroids, hematopoietic agents, antiplatelet agents, anticoagulants, coagulants, thrombolytic agents, hemorrheologic agents, hemostatics, plasma expanders, hormones, sex hormones, uterine-active agents, bisphosphonates, antidiabetic agents, glucose-elevating agents, growth hormones, thyroid hormones, inotropic agents, antiarrhythmic agents, calcium channel blockers, vasodilators, sympatholytics, antihyperlipidemic agents, vasopressors, angiotensin antagonists, sclerosing agents, anti-impotence agents, urinary alkanizers, urinary acidifiers, anticholinergics, diuretics, bronchodilators, surfactants, antidepressants, antipsychotics, antianxiety agents, sedatives, hypnotics, barbiturates, antiemetic agents, analgesics, stimulants, anticonvulsants, antiparkinson agents, proton pump inhibitors, $H_2$-antagonists, antispasmodics, laxatives, antidiarrheals, antiflatulents, digestive enzymes, gallstone solubilizing agents, antihypertensive agents, cholesterol-lowering agents, radiopaque agents, immune globulins, monoclonal antibodies, antibodies, antitoxins, antivenins, immunologic agents, anti-inflammatory agents, antineoplastic agents, alkylating agents, antimetabolites, antimitotic agents, radiopharmaceuticals, vitamins, herbs, trace elements, amino acids, enzymes, chelating agents, immunomodulatory agents and immunosuppressive agents; coating materials such as lubricants, and non-bioabsorbable substances such as silicone, beeswax, or polytetrafluoroethylene, as well as absorbable substances such as collagen, chitosan, chitin, carboxymethylcellulose, and homopolymers and/or copolymers of polyalkylene glycols, and higher fatty acids or salts or esters thereof, glycolic acid, a glycolide, lactic acid, a lactide, p-dioxanone, valerolactone and other lactones derived from linear aliphatic hydroxycarboxylic acids, α-hydroxybutyric acid, ethylene carbonate, ethylene oxide, propylene oxide, propylene carbonate, malic acid ester lactones, succinic acid, adipic acid and other linear aliphatic dicarboxylic acids, and linear aliphatic diols such as butanediol and hexanediol; wound healing agents; adhesives; sealants; blood products; blood components; preservatives; colorants; dyes; ultraviolet absorbers; ultraviolet stabilizers; photochromic agents; anti-adhesives; proteins; polysaccharides; peptides; genetic material; viral vectors; nucleic acids; nucleotides; plasmids; lymphokines; radioactive agents; metals; alloys; salts; growth factors; growth factor antagonists; cells; hydrophobic agents; hydrophilic agents; immunological agents; anti-colonization agents; diagnostic agents; imaging agents; diluents, such as water, saline, dextrose; and combinations thereof.

Turning now to FIG. 1, package 10 is shown including container 20 configured for receiving medical device 30 having passageway 35 defined therein and port 60 positioned on package 10 and connected to passageway 35 defined within medical device 30 for permitting the passage of an agent between the outside of container 20 and passageway 35. In some embodiments, an agent may be positioned within passageway 35 of medical device 30, e.g., a suture, prior to medical device 30 being received and stored within container 20. Port 60 is positioned on an outer edge of container 20 and is connected to the interior of medical device 30 via passageway 35.

It is envisioned that a delivery device may be connected to port 60 to deliver an agent through port 60 and into passageway 35 defined within medical device 30. Since passageway 35 is defined within at least a portion of medical device 30, the agent may coat, impregnate, react with, or be absorbed by medical device 30. In some embodiments, passageway 35 may be used to store the agent within medical device 30 to deliver the agent to the site of implantation.

Figure 2:
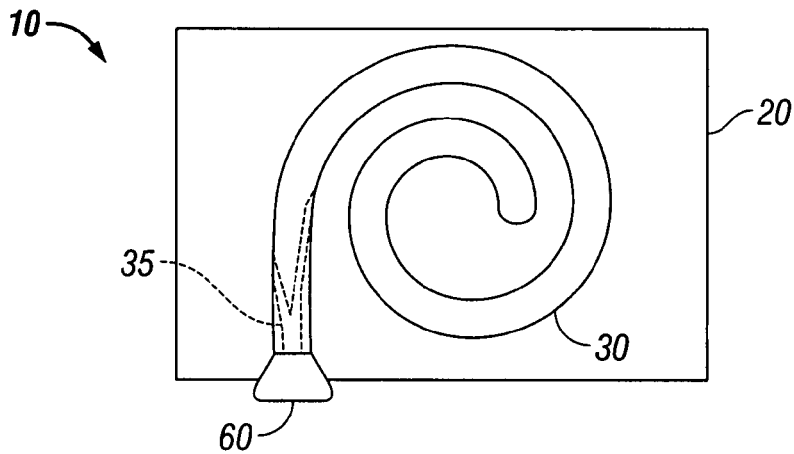
FIG. 2 is a top view of a medical device package as described herein.

In another embodiment, as shown in FIG. 2, package 10 is shown including container 20, port 60 and medical device 30 having passageway 35 defined therein. As shown, passageway 35 is defined within only a portion of medical device 30. In other embodiments, as shown in FIG. 1, passageway 35 may be defined within the entire length of medical device 30.

Figure 3:
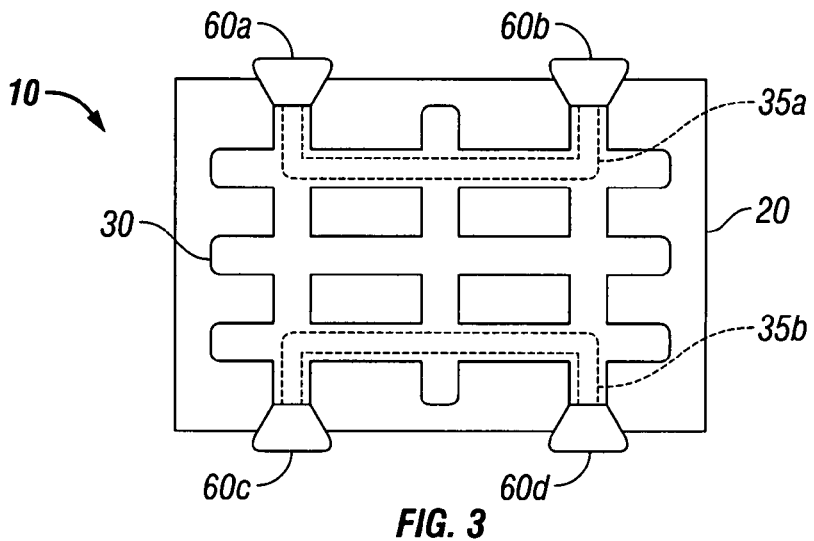
FIG. 3 is a side view of a medical device package as described herein.

Turning now to FIG. 3, container 20 is shown configured for receiving medical device 30 having more than one passageway 35a and 35b defined therein and more than one port 60a, 60b, 60c, 60d positioned on package 10. Ports 60a-b and 60c-d are connected to passageways 35a and 35b, respectively, in a multitude of locations thereby allowing the passage of at least one agent between the outside of container 20 and passageway 35. In some embodiments, different agents may be passed between different ports to coat, impregnate, react with, or be absorbed by different portions of medical device 30. It is envisioned that the medical device, e.g., a surgical mesh, may be coated with a first agent, e.g., an anti-adhesive agent on a first portion of the medical device and a second agent, e.g., an adhesive agent, on a second portion of the medical device. Following implantation, the first and second agents would reach the exterior of the medical device thereby enhancing tissue attachment on one side of the device and preventing tissue attachment on another side of the device.

In still another embodiment, the package in accordance with the present disclosure includes a container for receiving a medical device having a passageway defined therein and a single port positioned on the package and connected to multiple locations in the passageway for permitting the passage of an agent between the outside of the container and multiple locations within the passageway defined within the medical device.

It is well understood that various modifications may be made to the embodiments disclosed herein. Therefore, the above description should not be construed as limiting, but merely as exemplifications of particularly useful embodiments. Those skilled in the art will envision other modifications within the scope and spirit of the claims appended hereto.

What is claimed is:

1. A packaged medical device, said packaged device comprising:
   a surgical mesh having at least one hollow portion defined therein;
   a first cavity in a sealed package configured and dimensioned to receive said surgical mesh;
   at least one port attached to said package and attached to said at least one hollow portion defined within said surgical mesh for permitting the sterile passage of at least one agent between the outside of said sealed package and said at least one hollow portion defined within said surgical mesh.

2. The packaged medical device of claim 1 further comprising at least one agent.

3. The packaged medical device of claim 2 wherein said agent is selected from the group consisting of drugs, coating materials, wound healing agents, adhesives, sealants, blood products, blood components, preservatives, colorants, dyes, ultraviolet absorbers, ultraviolet stabilizers, photochromic agents, anti-adhesives, proteins, polysaccharides, peptides, genetic material, viral vectors, nucleic acids, nucleotides, plasmids, lymphokines, radioactive agents, metals, alloys, salts, growth factors, growth factor antagonists, cells, hydrophobic agents, hydrophilic agents, immunological agents, anti-colonization agents, diagnostic agents, imaging agents, radiopaque agents, and combinations thereof.

4. The packaged medical device of claim 1 said at least one port is removably attached to said package.

5. The packaged medical device of claim 1 said at least one port is removably attached to said surgical mesh.

6. A packaged suture, said packaged suture comprising:
   a suture having at least one hollow portion defined therein;
   a first cavity in a sealed package configured and dimensioned to receive said suture;
   at least one port attached to said package and attached to said at least one hollow portion defined within said suture for permitting the sterile passage of at least one agent between the outside of said sealed package and said at least one hollow portion defined within said suture.

7. The packaged suture of claim 6 further comprising at least one agent.

8. The packaged suture of claim 7 wherein said agent is selected from the group consisting of drugs, coating materials, wound healing agents, adhesives, sealants, blood products, blood components, preservatives, colorants, dyes, ultraviolet absorbers, ultraviolet stabilizers, photochromic agents, anti-adhesives, proteins, polysaccharides, peptides, genetic material, viral vectors, nucleic acids, nucleotides, plasmids, lymphokines, radioactive agents, metals, alloys, salts, growth factors, growth factor antagonists, cells, hydrophobic agents, hydrophilic agents, immunological agents, anti-colonization agents, diagnostic agents, imaging agents, radiopaque agents, and combinations thereof.

9. The packaged suture of claim 6 said at least one port is removably attached to said package.

10. The packaged suture of claim 6 said at least one port is removably attached to said suture.

\* \* \* \* \*